(12) United States Patent
Li (10) Patent No.: US 8,604,226 B2
(45) Date of Patent: Dec. 10, 2013

(54) PROCESS FOR PREPARING ALPHA-SULFO-FATTY ACID ESTER SALT SURFACTANTS

(75) Inventor: Hongcai Li, Shandong (CN)

(73) Assignee: Hongcai Li, Shangdong (CN)

(*) Notice: Subject to any disclaimer, the term of this patent is extended or adjusted under 35 U.S.C. 154(b) by 660 days.

(21) Appl. No.: 12/226,754

(22) PCT Filed: Apr. 24, 2007

(86) PCT No.: PCT/CN2007/001370
§ 371 (c)(1),
(2), (4) Date: Feb. 9, 2009

(87) PCT Pub. No.: WO2007/124686
PCT Pub. Date: Nov. 8, 2007

(65) Prior Publication Data
US 2009/0306418 A1    Dec. 10, 2009

(51) Int. Cl.
*C11D 1/28* (2006.01)
(52) U.S. Cl.
USPC ............................................................ 554/98
(58) Field of Classification Search
USPC ............................................................ 554/98
See application file for complete search history.

(56) References Cited

U.S. PATENT DOCUMENTS

| | | | | |
|---|---|---|---|---|
| 3,452,064 A | * | 6/1969 | Koch et al. | 554/94 |
| 3,997,575 A | | 12/1976 | Ogoshi | |
| 4,080,372 A | * | 3/1978 | Stein et al. | 554/96 |
| 4,990,288 A | * | 2/1991 | Piorr et al. | 554/97 |
| 5,319,117 A | * | 6/1994 | Fabry et al. | 554/98 |
| 5,587,500 A | | 12/1996 | Hovda | |
| 5,683,178 A | * | 11/1997 | Nakamoto et al. | 366/325.3 |

FOREIGN PATENT DOCUMENTS

| | | | | |
|---|---|---|---|---|
| CN | 1106795 A | | 8/1995 | |
| JP | 4117352 | * | 4/1992 | ............ C07C 303/06 |
| JP | 8170093 | * | 7/1996 | ............... C11D 1/28 |

OTHER PUBLICATIONS

JP4117352, Tozawa, M. Production of alpha-sulfofatty acid eser salt, 1992, English Abstract (1 page).*
JP8170093, Oowaku, Y., et al., Production fo granule of alpha-sulfofatty aid ester salt, 1996, English Abstract (1 page).*
Smith, F.D., et al., The alpha-sulfonatin of alkyl palmitates and stearates, 1967, Journal of the American Oil Chemists' society, vo. 44, No. 7, pp. 405-406 (2 pages).*
Stein, W., et al., alpha-Sulfonated Fatty Acids and Esters: Manufacturing process, properties and applicaitons, 1975, Journal of the American Oil Chemists' Society, vol. 51, No. 9, pp. 323-329 (7 pages).*
JP4117352, Process for producing alpha-sulfo fatty acid ester salt, 1992, English Translation, 12 pages.*
Written Opinion issued on Jun. 28, 2007, for International Patent Application No. PCT/CN2007/001370 filed on Apr. 24, 2007.
International Preliminary Report on Patentability issued on Oct. 28, 2008, for International Patent Application No. PCT/CN2007/001370 filed on Apr. 24, 2007.

* cited by examiner

*Primary Examiner* — Yate K Cutliff
(74) *Attorney, Agent, or Firm* — Ballard Spahr LLP (57) ABSTRACT

A process for preparing α-sulpho-fatty acid ester salt surfactant comprises: (1) sulphonating a fatty acid ester with $SO_3$ to produce a crude sulphonic acid, (2) bleaching the crude sulphonic acid from step (1) with hydrogen peroxide; (3) secondarily esterifying the product from step (2) with alcohol; (4) neutralizing the product from step (3) with an alkali solution; and (5) drying the product from step (4) to powder.

20 Claims, 7 Drawing Sheets

PROCESS FOR PREPARING ALPHA-SULFO-FATTY ACID ESTER SALT SURFACTANTS

CROSS REFERENCE TO RELATED APPLICATIONS

The present application is a National Phase Application of International Application No. PCT/CN2007/001370, filed Apr. 24, 2007, which claims priority to Chinese Patent Application No. 200610043643.X, filed Apr. 27, 2006, which applications are incorporated herein fully by this reference.

TECHNICAL FIELD

The present invention relates to the field of surfactant, and in particular, to a process for preparing alpha-sulfo-fatty acid ester salt surfactants.

BACKGROUND ART

Alpha-sulfo-fatty acid ester salts are valuable surfactants which have strong resistance to hard water and can be easily biodegraded. They can be used in daily chemical industry, ore dressing and the like.

The sulfonation of a fatty acid ester is often carried out in a falling film sulfonator by a reaction of the fatty acid ester and sulphur trioxide. The obtained sulfonic acid is often dark in color, which renders the appearance of the final product unacceptable. Therefore, the sulfonic acid is typically subjected to bleaching to make the product color as light as possible. The neutralized sulfonic acid is a paste product containing 30%-50% of the active compound, which is hard to be transported in a large amount and is not suitable to be prepared into a detergent in powder form. Thus, it is preferably dried into granules or powders before being directly formulated with other powdery materials. In addition, the sulfonation reaction inevitably generates an undesirable disodium (or dipotassium) salt. Thus, it is necessary to perform a reesterification in order to reduce the content of the di-salt as much as possible. In order to produce a satisfying alpha-sulfo-fatty acid ester salt, it is necessary to undergo the above steps.

Much efforts have been made on the sulfonation of fatty acid esters in previous processes. Free oil content and color, however, cannot be ensured at the same time. The product color will become dark if the content of free oil is reduced, while the content of the free oil will increase if the color is whitened. In the bleaching process, bleaching and reesterification are mostly carried out in one step, in which hydrogen peroxide (oxydol) is used as bleaching agent in an alcoholic system at a temperature above 90° C., see the Chinese patents No. CN 94115317.7, and CN 00133161.2. The temperature is much higher than the boiling point of the alcohol, which also facilitates the decomposition of hydrogen peroxide, thus rendering the system being recycled under high pressure. The process is also accompanied by some side reactions, which produce such as ethers and the like. The ethers are very dangerous since they are flammable and explosive, being hard to be disposed. In addition, a large amount of the alcohol has negative influence on the bleaching rate and effect. There are also attempts to bleach the sulfonic acid with hydrogen peroxide in a stainless steel equipment in a batch way. However, the bleaching reaction is difficult to control because of the highly viscous product and the rapid exotherm, which negatively affects the bleaching effect and the reproducibility of the product with good performance.

Due to high susceptibility to temperature and high viscosity of the alpha-sulfo-fatty acid ester salts, it is even difficult to dry them into solid form while the color and the disodium (or dipotassium) salt content are ensured.

Contents of the Invention

The object of the invention is to provide a new process for preparing alpha-sulfo-fatty acid ester salts, which is safe, easy to control and produces a product with satisfying color.

The present invention provides a process for preparing alpha-sulfo-fatty acid ester salt surfactants, which consists of the following steps:

(1) sulfonating a fatty acid ester with sulphur trioxide to prepare a crude sulfonic acid;
(2) bleaching the crude sulfonic acid obtained in step (1) by using hydrogen peroxide as bleaching agent;
(3) subjecting the product of step (2) to a secondary esterification using an alcohol as esterifying agent;
(4) neutralizing the product of step (3) with a base; and
(5) drying the product of step (4) to obtain a powdery product.

The process is carried out by employing one or more of the following means:

Means 1: a continuous bleach step at a low temperature.
Means 2: a secondary esterification step by adding a certain amount of alcohol.
Means 3: a neutralization step by using a base alcoholic solution (including a sodium (or potassium) alkoxide solution or a base in an alcohol), or a liquid base.
Means 4: a drying step in a rotating thin-film evaporator.

Preferably, the fatty acid methyl ester is sulfonated with sulphur trioxide in step (1) at a ratio of 1:1.15 to 1:1.35 (preferably 1:1.25) at a temperature between 75° C. and 85° C. (preferably 80° C.). The obtained sulfonic acid is subjected to a two-step aging, the first lasting for 40 to 60 minutes at 80° C.-90° C., and the secondary lasting for 30 to 60 minutes at 70° C.-80° C.

The obtained sulfonic acid is directly bleached with oxydol at a concentration of 25%-50% (preferably 35%). The amount of the oxydol used is 3%-20%, preferably 5%-10%, and more preferably 5%-8% based on the weight of the sulfonic acid.

Preferably, the reactants in step (2) are fed by means of spray.

Further preferably, the reactants in step (2) are mixed homogeneously in a rotor film-scrapping shear mixer.

Further preferably, the heat released during the bleaching in step (2) is removed by cool air blast or room-temperature air blast.

More preferably, the bleaching process is carried out in a continuous way at a temperature between 50° C. and 150° C., preferably between 75° C. and 90° C., by sequentially employing a spray mixing, a homogeneous mixing in a rotor film-scrapping shear mixer and an intensive air cooling step.

The bleached sulfonic acid is subjected to a secondary esterification (step (3)) using an alcohol as esterifying agent. The alcohol can be a $C_1$-$C_3$ alcohol, preferably methanol. The amount of the alcohol used is 75%-200%, preferably 75%-150%, and more preferably 100%, based on the total weight of the sulfonic acid (after bleaching). The secondary esterification is carried out under reflux for 1-6 hours.

In step (4), the sulfonic acid can be neutralized with an aqueous sodium (or potassium) hydroxide solution, an alcoholic sodium (or potassium) hydroxide solution or sodium (or potassium) alkoxide. The neutralization equipment and operation are similar to the bleaching step. Preferably, the base solution used in step (4) is an aqueous or alcoholic sodium hydroxide solution. The base concentration is 5%-50%, preferably 10%-30%. The neutralization temperature is in the range of 40° C.-80° C., preferably 50° C.-60° C.

Preferably, the reactants in step (4) are fed by means of spray.

Preferably, the reactants in step (4) are mixed homogeneously in a rotor film-scrapping shear mixer.

Preferably, the heat released from the neutralization step (4) is removed by cool air blast or room-temperature air blast.

The paste product obtained after neutralization is dried in a rotary thin-film evaporator under vacuum pressure of 50-200 mmHg at a temperature between 50° C. and 90° C.

The preparation process of the present invention is safe, easy to operate and control, and can produce a product with good reproducibility. The product in improved color has a desirable low content of the disodium (dipotassium) salt with little harmful substance retained.

BRIEF DESCRIPTION OF FIGURES

The components shown in FIGS. 4 and 5 are combined to a primary rotor film-scrapping shear mixer. The stage number of the rotor film-scrapping shear mixer is generally in the range of 3-50, depending on the condition of the reaction.

MODE OF CARRYING OUT THE INVENTION

Figure 1:
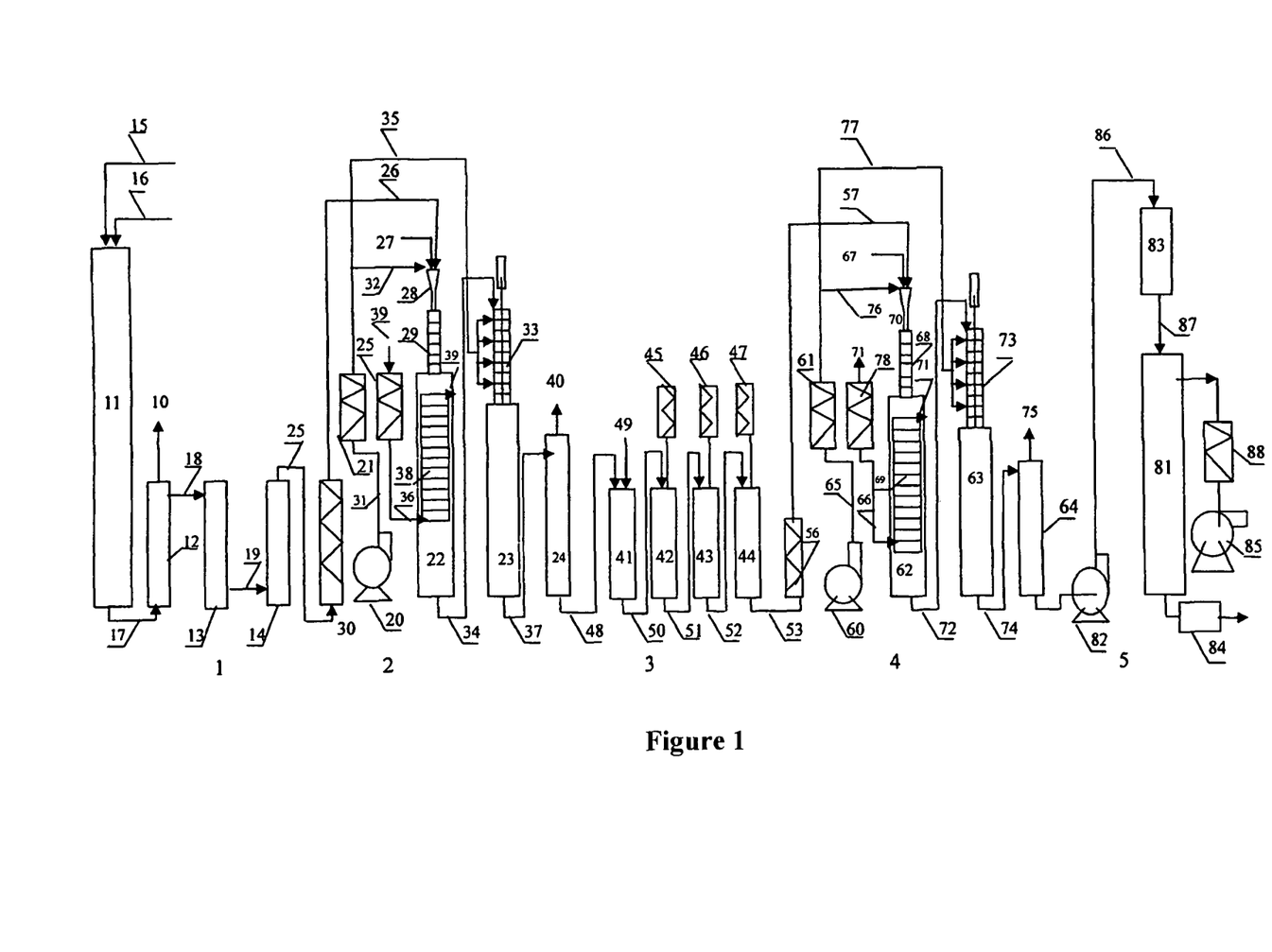
FIG. 1 is a process flow chart showing the inventive preparation of alpha-sulfo-fatty acid ester salts, which process comprises five steps, i.e. sulfonation, bleaching, secondary esterification, neutralization and drying.

With reference to FIG. 1, the process of the present invention consists of five steps: (1) sulfonation; (2) bleaching; (3) secondary esterification; (4) neutralization; and (5) drying.

The sulfonation unit consists of a falling film sulfonator 11, a gas-liquid separator 12 and aging reactors 13 and 14. A mixture of air and sulphur trioxide from a pipe 15 and a fatty acid ester from a pipe 16 are fed to the sulfonator 11. A reaction mixture exits the sulfonator and enters the gas-liquid separator 12 through a pipe 17. The separated gas is discharged via 10 for further absorption treatment. The liquid sulfonic acid is fed to the aging reactor 13 through a pipe 18, and stays there for a time period before being fed to the aging reactor 14 through a pipe 19.

Figure 2:
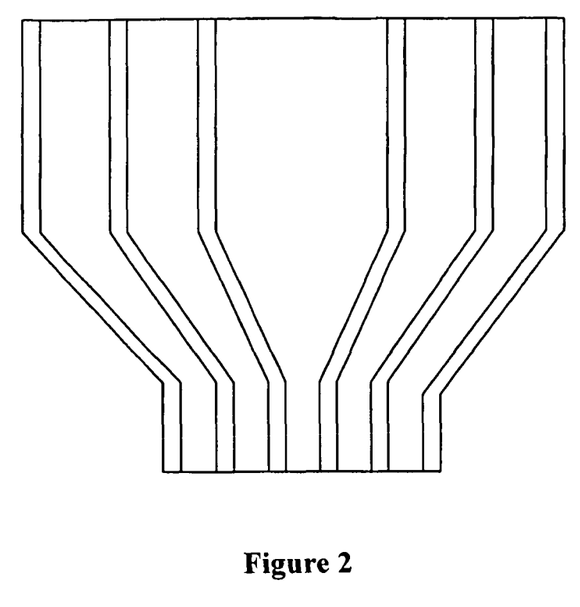
FIG. 2 is a schematic diagram showing a spray header used in the present invention.
Figure 3:
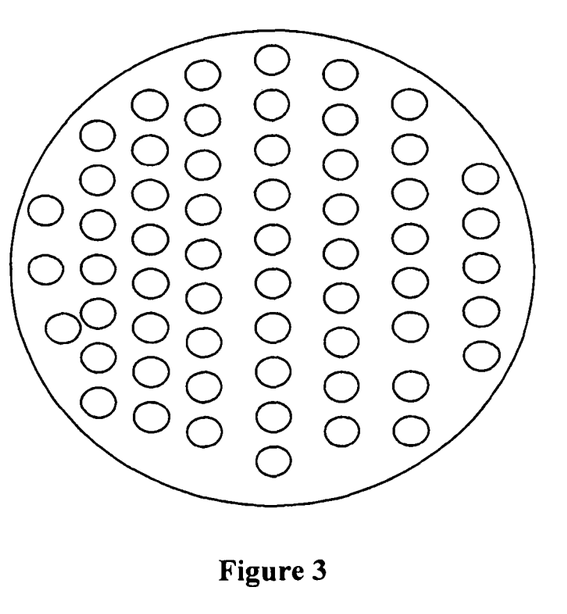
FIG. 3 is a schematic diagram showing a perforated plate used in the present invention.
Figure 4:
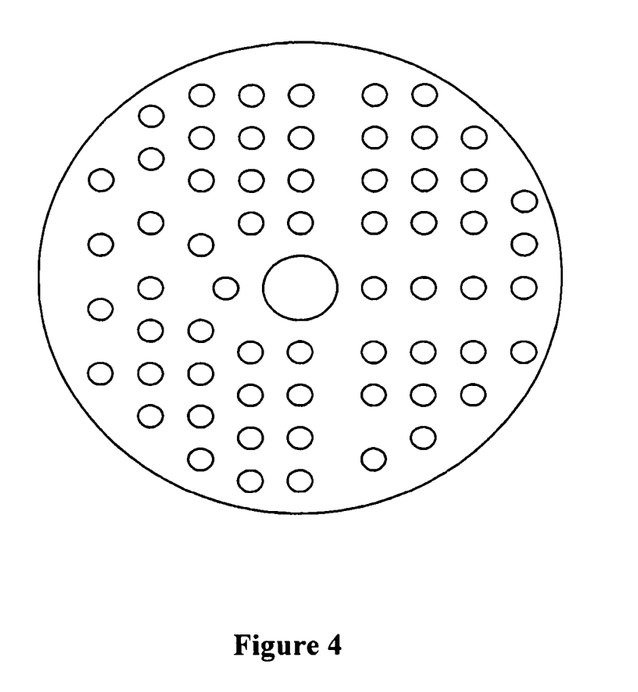
FIG. 4 is a schematic diagram showing a stator air plate used in the present invention.
Figure 5:
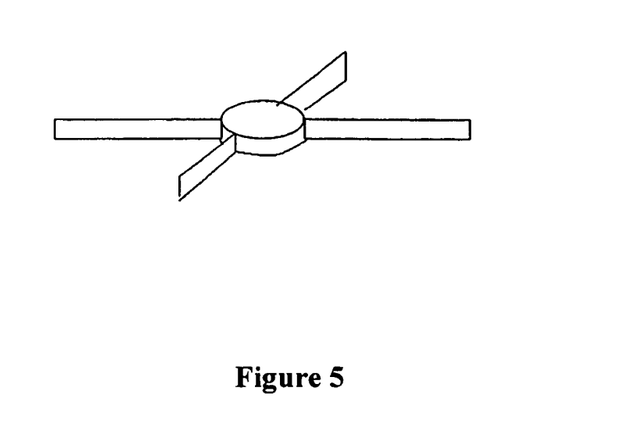
FIG. 5 is a schematic diagram showing a rotor film-scrapping blade used in the present invention.

The bleaching unit consists of a fan 20, freezers 21 and 25, a primary mixing tank 22, a secondary mixing tank 23 and a gas-mass separator 24. The sulfonic acid from the aging reactor 14 is transported through a pipe 25 to a heat exchanger 30 for cooling. Air from the fan 20 is fed through a pipe 31 to the freezer, where it is cooled down, and then enters a spray header 28 through a pipe 32 and a multi-stage rotor film-scrapping shear mixer 33 through a pipe 35. Hydrogen peroxide from a pipe 27, the sulfonic acid from a pipe 26 and the air from the pipe 32 are spray-mixed in the spray header of the primary mixing tank, and then cooled down by passing through a multi-stage perforated plate 29 and a lower tube array 38 (wherein the cooling medium is recycled through pipes 36 and 39). The cooled mixture is then transported into the secondary mixing tank 23 through a pipe 34 and mixed homogeneously by the multi-stage rotor film-scrapping shear mixer 33. The reaction mixture is then transported through a pipe 37 to the gas-mass separator 24, in which the air is discharged from 40 to obtain a paste product.

The secondary esterification unit consists of a mixer 41, reactors 42, 43 and 44, and condensers 45, 46 and 47. The bleached sulfonic acid from a pipe 48 and methanol from a pipe 49 are fed together to the mixer 41. The mixture is heated and sent successively to the reactors 42, 43 and 44 through pipes 50, 51 and 52, respectively, for the secondary esterification. The evaporated methanol is refluxed by the condensers 45, 46 and 47. The secondary esterification is carried out in a continuous way, i.e., the reactant materials are fed in continuously from the top of the reactor, and the product materials are discharged continuously from the bottom of the reactor. The product is finally sent through a pipe 53 to a cooler 56 for cooling.

The neutralization unit consists of a fan 60, freezers 61 and 78, a primary mixing tank 62, a secondary mixing tank 63 and a gas-mass separator 64. The esterified sulfonic acid is cooled down in the heat exchanger 56. Air from the fan 60 is sent through a pipe 65 to the freezer, where it is cooled down, and then sent through a pipe 76 to a spray header 70 of the primary mixing tank, along with an alkali liquid from a pipe 67 and the sulfonic acid from a pipe 57. The mixture is spray-mixed and further cooled down by passing through a multi-stage perforated plate 68 and a lower tube array 69 (wherein the cooling medium is recycled through pipes 66 and 71). The cooled mixture is then transported through a pipe 72 to the secondary mixing tank 63, in which it is preferably mixed homogeneously by a multi-stage rotor film-scrapping shear mixer 73 with cooling by the cooled air from a pipe 77. The mixture is finally transported through a pipe 74 to the gas-mass separator 64, in which the air is discharged from 75 to obtain a paste product.

The drying step in the invention is carried out in a rotary thin-film evaporator. The drying unit consists of a rotary thin-film evaporator 81, a conveying pump 82, a storage tank 83, a screw discharging machine 84, a vacuum pump 85 and a condenser 88. The neutralized paste is sent to the storage tank 83 through a pipe 86 and then to the drying vessel through a pipe 87. The dried product is discharged through the screw discharging machine 84.

The first step of the inventive process comprises sulfonating a fatty acid ester having the following formula:

in which R is $C_4$-$C_{20}$ (preferably $C_{12}$-$C_{18}$ alkyl), and $R_1$ is $C_1$-$C_3$ (preferably $C_1$-$C_2$).

At first, sulphur trioxide is added to the fatty acid ester to form an intermediate (II) which can be a mixed anhydride, or an adduct, but which is definitely not a sulfonate:

The formation of the intermediate (II) activates the carbon atom alpha to the carbonyl group, which thus allows free $SO_3$ to react to form another intermediate (III) as shown below which is both a sulfonate and an $SO_3$ adduct or mixed anhydride:

The intermediate (III) undergo slow elimination of $SO_3$ to form the alpha-sulfo methyl ester (4) and free $SO_3$. The released $SO_3$ is available to react with the fatty acid methyl ester (I) or the intermediate (II) in a final step:

In order to convert most of the compound of formula (I) into a compound of formula (IV), sufficient excess $SO_3$ must be added to produce significant amounts of the intermediate (III), which slowly generates the needed free $SO_3$ to drive the sulfonation reaction to completion. Therefore, the mole ratio of the raw materials in the sulfonation reaction is preferably about 1:1.15 to 1:1.35.

The sulfonation process is accompanied by side reactions, such as a reaction between an alkene containing an unsaturated bond and sulphur trioxide to form a sultone, a di-sulfo compound and other color substances.

After the aging of the sulfonic acid for a time period, large amounts of the intermediate (III) are still present. The neutralization with an alkali or the bleaching with oxydol will cause the hydrolysis of the ester group:

in the presence of oxydol:

in the presence of sodium hydroxide:

The compound (IV) is the alpha-sulfo-fatty acid ester product which contains an amount of a disodium (or dipotassium) salt (V). Thus, the secondary esterification is necessary to reduce the formation of the di-salt. In the presence of an alcohol, a reesterification is carried out:

In the neutralization system, the hydrolysis rate is much higher when the local concentration of the base is too high, or at pH levels above 9. Therefore, very rapid and intimate mixing of the sulfonic acid and the alkali liquid are required during the neutralization to avoid creating high local pH values and high temperatures which can lead to excessive hydrolysis.

Sulfonation

With reference to FIG. 1, the sulfonation step in an embodiment of the inventive process is carried out in a unit which consists of a falling film sulfonator 11, a gas-liquid separator 12 and aging reactors 13 and 14.

A mixture of air and sulphur trioxide from a pipe 15 and a fatty acid ester from a pipe 16 are fed to the sulfonator 11. A reaction mixture exits the sulfonator and enters the gas-liquid separator 12 through a pipe 17. The liquid sulfonic acid is fed to the aging reactor 13 through a pipe 18, and stays there for a time period before being fed to the aging reactor 14 through a pipe 19.

The sulfonation is a key step in the preparation process of the alpha-sulfo-fatty acid ester salts. The main index, which involve free oil, by-products and color, are interrelated with each other. The low sulfonation level produces a product in light color with low content of by-products, but may result in the increased content of free oil. The high sulfonation level decreases the content of free oil, but may produce a dark product containing large amounts of by-products. Of the three index, the content of free oil shall be primarily considered, while the others are the secondary concerns. The important sulfonation conditions include the ratio of the raw materials (ester to sulphur trioxide and air to sulphur trioxide), the sulfonation temperature and the aging time and temperature.

The preferred sulfonation conditions of the invention are as follows: the mole ratio of the fatty acid ester to sulphur trioxide being 1:1.15-1:1.35; the sulfonation temperature being in the range of 75° C.-85° C. (preferably 80° C.); the first aging at a temperature between 80° C. and 90° C. for 40-60 minutes, and the secondary aging at a temperature between 70° C. and 80° C. for 30-60 minutes.

Bleaching

The bleaching step in the inventive process can be carried out in a reaction system as shown in FIG. 1. The system is a continuous processing unit, in which the bleaching step can be completed at a low temperature in a relatively short time period. The bleaching effect mainly depends on the temperature, the amount of the bleaching agent, the bleaching time and the like, of which the temperature is the most important factor. The bleaching reaction is rapid and highly exothermic, and thus is difficult to control. The initial temperature is also critical. If the temperature is too low, the reaction will be carried out at a slow rate with the poor bleaching effect. If the initial temperature is too high, the reaction will start rapidly, while generating large amounts of heat, which cannot be removed, in a short time period, and also the bleaching effect will be deteriorated. Therefore, it is critical to control the temperature and remove the reaction heat in time, to achieve the satisfying bleaching effect.

Theoretically, many oxidizing agent, such as sodium hypochlorite, hydrogen peroxide, ozone and the like, can be used as bleaching agent. Sodium hypochlorite solution contains large amounts of water and thus has low effective concentration. The more the water is contained, the more the reaction heat will be released, which is unfavorable for the reaction. Ozone with a simple composition has a strong oxidizing ability. However, it is always produced in a small amount, which cannot meet the requirement for large scale production. Hydrogen peroxide is relatively suitable as bleaching agent owing to its strong oxidizing ability, the simple water product after decomposition, and low cost. It is thus preferably used as bleaching agent in the invention.

The experiments show that the bleaching manner employed is more important. The sulfonic acid turns into a semi-solid in the presence of water. The semi-solid has a high viscosity even at a relatively high temperature, making the mass transfer difficult even in the presence of large amounts of an alcohol. In the unit of the invention, the bleaching is carried out continuously at a low temperature with a rapid rate. Considering that a large amount of reaction heat may be released, the chamber of the mixer is cooled down intensively by injecting a large amount of air as cold medium in a short time period.

With reference to FIG. 1, the bleaching unit consists of a fan 20, freezers 21 and 25, a primary mixing tank 22, a secondary mixing tank 23 and a gas-mass separator 24.

The sulfonic acid from the aging reactor 14 is transported through a pipe 25 to a heat exchanger 30 for cooling. Air from the fan 20 is fed through a pipe 31 to the freezer, where it is cooled down, and then enters a spray header 28 through a pipe 32 and a multi-stage rotor film-scrapping shear mixer 33 through a pipe 35. Hydrogen peroxide from a pipe 27, the sulfonic acid from a pipe 26 and the air from the pipe 32 are spray-mixed in the spray header of the primary mixing tank, and then cooled down by passing through a multi-stage perforated plate 29 and a lower tube array 38. The cooled mixture is then transported into the secondary mixing tank 23 through a pipe 34 and mixed homogeneously by the multi-stage rotor film-scrapping shear mixer 33. The reaction mixture is then transported through a pipe 37 to the gas-mass separator 24, in which the air is discharged from 40 to obtain a paste product. The temperature of the bleaching step is in the range of 50° C.-150° C., preferably 75° C.-90° C.

With reference to FIGS. 6-10, a commercial oxydol has a concentration of 25%, 35%, 50% or 70%. The experiments show that the bleaching effect is poor when using dilute oxydol; the color, however, will be dark if the concentration is too high. The concentration of oxydol used in the invention is 25%-50%, preferably 35%.

The amount of oxydol used will also greatly affect the bleaching effect. The experiment results show that excessive or deficient oxydol is unfavourable for the bleaching, which is consistent with the principle. If a small amount of the bleaching agent is used as dilute solution, the insufficient oxidizing ability will deteriorate the bleaching effect. If a too large amount of the bleaching agent is used at a high concentration, the excessive oxidization may produce large amounts of by-products, which complicate the product composition, and also deteriorate the bleaching effect. Therefore, it is very important to suitably select the amount of the bleaching agent. The amount of oxydol used in the invention is 3%-20%, preferably 5%-10% and more preferably 5%-8% based on the weight of the sulfonic acid.

The direct bleaching of the sulfonic acid with oxydol in the invention produces less by-products, and decreases the system pressure and temperature, thus making the operation much safer. The slightly excess oxydol, which may remain after bleaching, can be removed in the subsequent steps.

Secondary Esterification

The special sulfonation mechanism of a fatty acid ester inevitably generates an undesirable disodium (or dipotassium) salt; and some di-salts may also form during the bleaching step. The problem can be solved by a secondary esterification in the presence of large amounts of an alcohol. The experiment results show that the secondary esterification is mainly affected by the amount of methanol used and the reaction time, in which an additional acid catalyst is not needed since the reaction system per se is highly acidic. The secondary esterification is also affected negatively by water generated in the system during the bleaching step. Therefore, the minimized addition amount of oxydol in the bleaching step is also necessary for this step. The esterification process has insignificant effect on the free oil content and the product color, which indicates that the sulfonic acid is stable during the esterification process.

With reference to FIG. 1, the secondary esterification unit consists of a mixer 41, reactors 42, 43, 44, and condensers 45, 46, 47.

The bleached sulfonic acid from a pipe 48 and methanol from a pipe 49 are fed together to the mixer 41. The mixture is heated and sent successively to the reactors 42, 43 and 44 through pipes 50, 51 and 52, respectively, for the secondary esterification. The evaporated methanol is refluxed by the condensers 45, 46 and 47. The secondary esterification is carried out in a continuous way, i.e., the reactant materials are fed in continuously from the top of the reactor, and the product materials are discharged continuously from the bottom of the reactor. The product is finally sent through a pipe 53 to a cooler 56 for cooling.

The high proportion of the alcohol in the esterification can accelerate the reaction, while being disadvantageous to the subsequent drying treatment. Therefore, the amount of alcohol must be appropriate. Methanol is preferably used in the invention in an amount of 75%-200% (preferably 100%), based on the weight of the sulfonic acid. The longer the esterification lasts, the lower the content of the disodium (dipotassium) salt will be. Thus, the reaction time depends on the requirement for the product quality, wherein a reaction generally for 1-6 hours can reduce the content of the disodium (dipotassium) salt to about 5%.

Neutralization

The neutralization after the sulfonation in the invention is carried out by reacting the sulfonic acid with a liquid hydroxide, such as sodium hydroxide or potassium hydroxide. The solvent may be either water or an alcohol. Considering that the secondary-esterified mass materials containing large amounts of an alcohol will be dried and purified in the subsequent steps, an alcohol is more preferably used. Either an alcoholic solution of hydroxide or a sodium (potassium) alkoxide solution can be used in the neutralization. The neutralization in the invention is carried out with a 5%-50% alcoholic solution of sodium (potassium) hydroxide at a temperature between 40° C. and 80° C., preferably between 50° C. and 60° C. The neutralized sulfonate salt is controlled to the pH in the range of 7-8.

With reference to FIG. 1, the mass materials exiting the heat exchanger 56 through a pipe 57 is neutralized with a base alcoholic solution (including a sodium alkoxide solution or a base in alcohol) or a liquid base in the neutralization step.

The neutralization unit consists of a fan 60, freezers 61 and 78, a primary mixing tank 62, a secondary mixing tank 63 and a gas-mass separator 64.

The esterified sulfonic acid is cooled down in the heat exchanger 56. Air from the fan 60 is sent through a pipe 65 to the freezer, where it is cooled down, and then sent through a pipe 76 to a spray header 70 of the primary mixing tank, along with an alkali liquid from a pipe 67 and the sulfonic acid from a pipe 57. The mixture is spray-mixed and further cooled down by passing through a multi-stage perforated plate 68 and a lower tube array 69. The cooled mixture is then transported through a pipe 72 to the secondary mixing tank 63, in which it is mixed homogeneously by a multi-stage rotor film-scrapping shear mixer 73 with cooling by the cooled air from a pipe 77. The mixture is finally transported through a pipe 74 to the gas-mass separator 64, in which a paste product is obtained.

The neutralization is preferably carried out at a temperature between 40° C. and 80° C.

Drying

The heated alpha-sulfo-fatty acid ester salts turn into a highly viscous semi-solid with poor flowability. The drying at a high temperature can produce a dark product containing an increased amount of the disodium (dipotassium) salt.

The drying in the invention is carried out in a rotary thin-film evaporator. The drying unit consists of a rotary thin-film evaporator 81, a conveying pump 82, a storage tank 83, a screw discharging machine 84, a vacuum pump 85 and a condenser 88.

The neutralized paste is sent to the storage tank 83 through a pipe 86 and then to the dryer 81 through a pipe 87. The dried product is finally discharged through the screw discharging machine 84.

The drying in the invention is carried out at vacuum pressure of 50-200 mmHg at a temperature between 50° C. and 80° C.

In the bleaching and neutralization units according to the invention, the mass materials and air are sprayed out simultaneously by the spray mixing header. This can produce the mass materials in the form of spraying mist in the mixing chamber, thus increasing the contact area, achieving the homogeneous and rapid mixing. In addition, when the mass materials pass each stage of the perforated plate, air stream is generated to create an addition stirring action, which enhances the mixing and the reaction. Moreover, the relative motion between the stator air plate and the rotor film-scrapping blade makes the mass materials undergo repeated shear and surface breaking, thus making the mixing more sufficiently and facilitating the removal the reaction heat.

The present invention is further described in detail with reference to the following examples. However, they shall not be considered as limitation to the present invention.

Example 1

The Preparation of a Sodium Salt of an Alpha-Sulfo-Fatty Acid Methyl Ester

Raw Materials
1. Fatty Acid Methyl Ester: Self-Prepared
Main technical index:
(1) Distribution of carbon chain:
C14 2%
C16 81%
C18 17%
(2) Average molecular weight: 377
(3) Iodine value: <0.3 $gI_2$/100 g
(4) Acid value: <1.0 mgKOH/g
(5) Unsaponifiable components: <1.0%
(6) Saponification value: 198 mgKOH/g
2. Sulfur trioxide: prepared by sulphur combusting
3. Oxydol: industrial grade 33%
4. Methanol: industrial grade
5. Sodium hydroxide: industrial grade, 98%

Method

With reference to FIG. 1, a falling-film sulfonator 12 consisted of fourteen sulfonating tubes with an inner diameter of 30 mm and a length of 6000 mm. A liquid fatty acid methyl ester from a pipe 16 was distributed homogeneously on the wall of each sulfonating tube. A mixture of sulphur trioxide and air was injected into each sulfonating tube and flew downward along the tube together with the liquid, during which process the fatty acid ester and sulphur trioxide were reacted. The sulfonic acid mixture exited from the bottom of the reactor and entered a gas-liquid separator 12 through a pipe 17, where the remaining gas was separated for an absorption by an alkali liquor in a high-pressure electrostatic demister. The sulfonic acid liquid flew through a pipe 18 into an aging reactor 13, where it was aged at 80° C.-90° C. for 40 minutes, and then through a pipe 19 to another aging reactor 14, where it was aged at 70° C.-80° C. for 30-40 minutes.

The aged sulfonic acid was then subjected to a bleaching step. The sulfonic acid from a pipe 26, oxydol from a pipe 27 and cold air from a pipe 35 were transported to a primary mixing tank 22 and a secondary mixing tank 23 for bleaching. The bleaching was carried out at a low temperature with oxydol (33% concentration) in an amount of about 8% based on the weight of the sulfonic acid. The oxydol and the sulfonic acid were injected by two metering pumps, respectively.

The bleached sulfonic acid was then subjected to a secondary esterification. The sulfonic acid from a pipe 48 and methanol from a pipe 49 were transported to a mixer 41, where the sulfonic acid was dissolved and heated to 60° C. The heated mixture was then sent via pipes to reactors 42, 43 and 44 successively, where the esterification was carried out under reflux at about 80° C. The reaction began when the mass materials entered the feed port on the top of the reactor, and stopped when the mass materials exited the discharge port at the bottom of the reactor. The reaction was carried out in a continuous way.

Neutralization: The liquid mixture of the sulfonic acid and methanol and a 15% solution of sodium hydroxide in methanol were charged via metering pumps into a primary mixing tank 62 and a secondary mixing tank 63 for the neutralization. The reaction was carried out until a pH value of 7-8.

Drying: The obtained paste product was transported by a screw pump to a storage tank at the top of a rotary thin-film evaporator, and driven by vacuum suction into an evaporator. The dried mass, which piled at the bottom of the evaporator, was discharged through a screw discharging equipment, and then cooled before being ground by a grinder.

The process parameters in the test are shown in table 1.

| Material | Molecular weight | Gas feedstock (15) | Liquid feedstock (16) | Outlet of the reactor (12) | Discharging port (10) | Outlet of the aging reactor (13) | Outlet of the aging reactor (14) | oxydol (26) |
| --- | --- | --- | --- | --- | --- | --- | --- | --- |
| Air | 28 | 2000 | | 0 | | | | |
| $SO_3$ | 80.1 | 102 | | 0 | | | | |
| $SO_2$ | 54.1 | 1.25 | | 3.6 | 1.2 | 2.5 | | |
| Fatty acid methyl ester | 274 | | 270 | 54 | 0.15 | 25.0 | 7.2 | |
| Adduct of sulfonic acid and $SO_3$ | 434 | | | 68.8 | 0.1 | 57.2 | 41.0 | |
| Sulfonic acid | 354 | | | 224 | 0.1 | 275.0 | 311.5 | |
| Sulfo-carboxylic acid | 340 | | | | | | | |
| Sodium sulfonate | 376 | | | | | | | |
| Disodium salt | 398 | | | | | | | |
| Oxydol | 34 | | | | | | | 28 |
| Methanol | 32 | | | | | | | |
| Sodium hydroxide | 40 | | | | | | | |
| Sodium sulfate | 142 | | | | | | | |
| Water | 18 | | | | | | | |
| Others | | | | | | | | |
| Temperature (° C.) | | | | 85 | | 80-90 | 70-80 | 26 |
| Time (min) | | | | | | 40-60 | 30-60 | |

| Material | Outlet of the bleaching unit (36) | methanol (37) | Outlet of the secondaryary esterification unit (44) | Sodium hydroxide | Base alcoholic solution (45) | Outlet of the neutralization unit (46) | powder (50) |
| --- | --- | --- | --- | --- | --- | --- | --- |
| Air | | | | | | | |
| $SO_3$ | 0.00 | | | | | | |
| $SO_2$ | 0.00 | | | | | | |
| Fatty acid methyl ester | 7.5 | | 7.5 | | | 7.6 | 7.6 |
| Adduct of sulfonic acid and $SO_3$ | 0 | | 0 | | | 0 | 0 |
| Sulfonic acid | 302.5 | | 328.1 | | | | 0 |
| Sulfo-carboxylic acid | 40.2 | | 15.8 | | | | 0 |
| Sodium sulfonate | | | | | | 346.7 | 345.2 |
| Disodium salt | | | | | | 20.0 | 21.6 |
| Oxydol | | | | | | | |
| Methanol | | 380.0 | | | | | |
| Sodium hydroxide | | | | 41.0 | 273.0 | | |

-continued

|  |  |  |  |  |  |  |  |
|---|---|---|---|---|---|---|---|
| Sodium sulfate |  |  |  |  |  | 28.0 | 28.0 |
| Water |  |  |  |  |  |  | 12.9 |
| Others |  |  |  |  |  |  | 13.2 |
| Temperature (° C.) | 70-85 | 26 | 80 | 26 | 26 | 65 |  |
| Time (min) | 1-5 |  | 60-360 |  |  | 1-5 |  |

Example 2

Bleaching Test

The sulfonic acid, the test equipment and the process employed in this example were the same as example 1. The continuous bleaching was carried out using oxydol as bleaching agent in a liquid mixing pump, to test the effect of the reaction temperature on the bleaching result.

A 35% oxydol was used in an amount of 8% based on the weight of the sulfonic acid. The bleaching was carried out for about 1-5 minutes at a temperature of 50° C., 60° C., 75° C., 90° C., 120° C. and 150° C., respectively.

Figure 6:
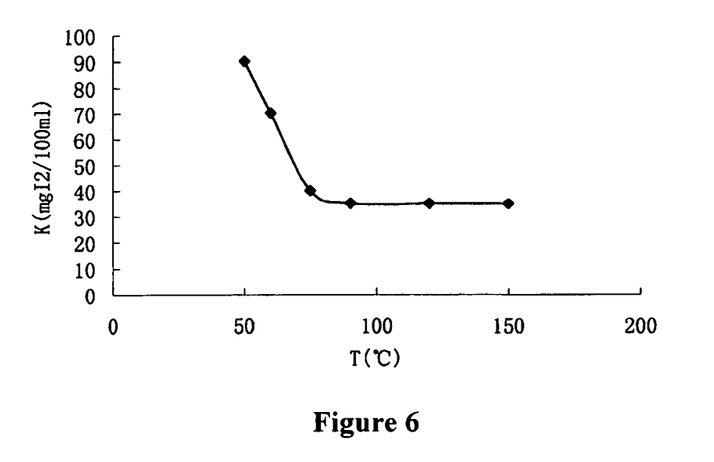
FIG. 6 shows the color of the bleached sulfonic acid in example 2 with oxydol at 50° C., 60° C., 75° C., 90° C., 120° C. and 150° C., respectively, wherein T (° C.) is the bleaching temperature and K ($mgI_2$/100 ml) is the color.

The color was evaluated by a visual colorimetry using a potassium iodide-iodine standard solution (the same below). The sample was diluted to an alcoholic solutions containing 5% of the active substance. The color of sample was expressed as color index of iodine, which is represented by the amount of free iodine in mg contained in 100 ml of the potassium iodide-iodine standard solution. The result is shown in FIG. 6.

The experiment result shows that the low temperature slows down the bleaching reaction and produces a relatively dark product, while the temperature above 75° C. can accelerate the bleaching with the improved bleaching effect. The temperature between 75° C. and 150° C. has insignificant influence on the product color.

Example 3

Bleaching Test

The sulfonic acid, the test equipment and the process employed in this example were the same as example 1. The continuous bleaching was carried out using oxydol as bleaching agent in a liquid mixing pump, to test the effect of the oxydol concentration on the bleaching result.

Figure 7:
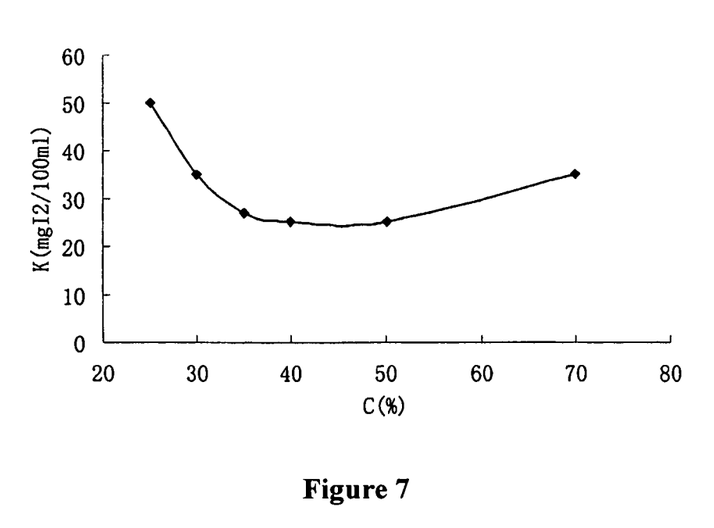
FIG. 7 shows the color of the bleached sulfonic acid in example 3 at 85° C. with oxydol at a concentration of 25%, 30%, 35%, 40%, 50% and 70%, respectively, wherein C (%) is the concentration and K ($mgI_2$/100 ml) is the color.

Oxydol was added in an amount of 2% (the amount of pure hydrogen peroxide) based on the weight of the sulfonic acid, with a test concentration of 25%, 30%, 35%, 40%, 50% and 70%, respectively. The bleaching was carried out for 1-5 minutes at 85° C. The result is shown in FIG. 7.

The experiment result shows that the bleaching effects are slightly poor when oxydol with a concentration of 25% or 70% is used. The high concentration of oxydol makes the reaction vigorous, which may be accompanied by side reactions, resulting in deteriorated bleaching effect.

Example 4

Bleaching Test

The sulfonic acid, the test equipment and the process employed in this example were the same as example 1. The continuous bleaching was carried out using oxydol as bleaching agent in a liquid mixing pump, to test the effect of the amount of oxydol used on the bleaching result.

Figure 8:
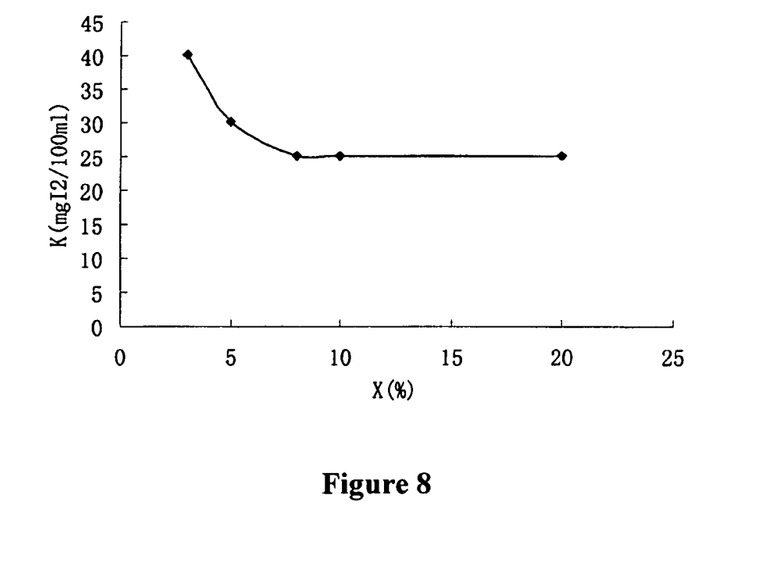
FIG. 8 shows the color of the bleached sulfonic acid in example 4 at 85° C. with a 35% oxydol in an amount of 3%, 5%, 8%, 10% and 20%, respectively, based on the weight of the sulfonic acid, wherein X (%) is the weight percent of oxydol and K ($mgI_2$/100 ml) is the color.

A 35% oxydol was added in an amount of 3%, 5%, 8%, 10% and 20%, respectively, based on the weight of the sulfonic acid. The bleaching was carried out for 1-5 minutes at 85° C. The result is shown in FIG. 8.

The experiment result shows that the oxydol is preferably added in an amount of 5%-10% based on the weight of the sulfonic acid.

Example 5

Bleaching Test

The sulfonic acid, the test equipment and the process employed in this example were the same as example 1. The continuous bleaching was carried out using oxydol as bleaching agent in a liquid mixing pump, to test the effect of the reaction temperature on the content of disodium salt.

Figure 9:
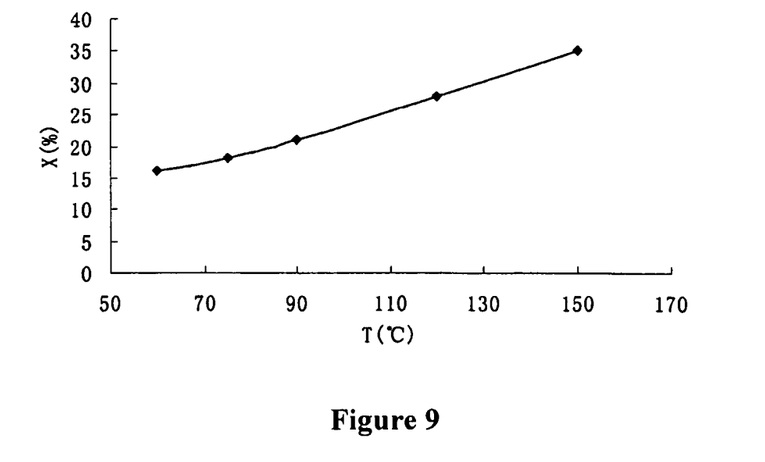
FIG. 9 shows the content of the disodium salt in example 5 in the bleached sulfonic acid with oxydol at 60° C., 75° C., 85° C., 120° C. and 150° C., respectively, wherein T (° C.) is the temperature and X (%) is the content of the disodium salt.

A 35% oxydol was added in an amount of 8% based on the weight of the sulfonic acid. The bleaching was carried out for about 1-5 minutes at a temperature of 50° C., 60° C., 75° C., 90° C., 120° C. and 150° C., respectively. The result is shown in FIG. 9.

The experiment result shows that the high temperature results in increased amounts of the disodium salt. Thus, the bleaching temperature shall be as low as possible.

Example 6

Secondary Esterification Test

The sulfonic acid, the test equipment and the process employed in this example were the same as example 1. The effect of the amount of an alcohol used in the secondary esterification on the content of the disodium salt was studied in the test.

Figure 10:
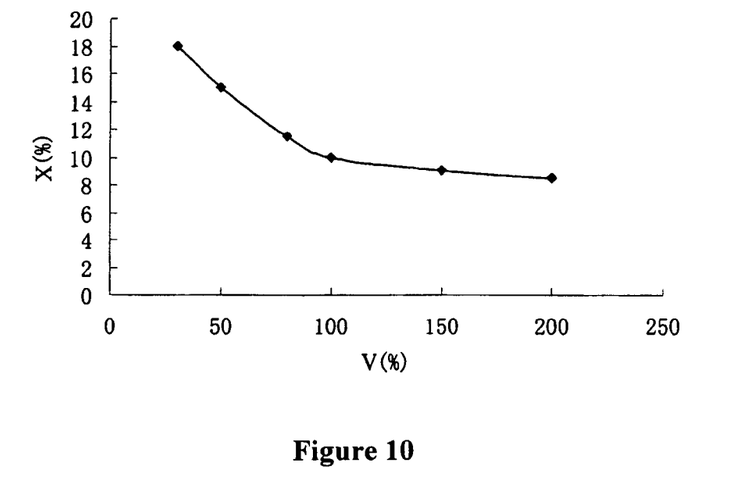
FIG. 10 shows the effect of the amount of the esterifying agent on the content of the disodium salt in the product in example 6, in which the amount of the esterifying agent used is 30%, 50%, 75%, 100%, 150% and 200%, respectively, based on the weight of the sulfonic acid. V (%) is the percent of the esterifying agent based on the weight of the sulfonic acid, and X (%) is the content of the disodium salt.

Methanol was used as esterifying agent in an amount of 30%, 50%, 75%, 100%, 150% and 200, respectively, based on the weight of the sulfonic acid (bleached). The esterification was carried out at a reflux temperature for 2 hours. The result is shown in FIG. 10.

The experiment result shows that a large amount of alcohol is advantageous to the esterification, while the addition amount above 80% has insignificant effect on the content of the disodium salt. In addition, excessive methanol may make the subsequent drying difficult. Thus, it is suitable to add the alcohol in an amount of 75%-150% based on the weight of the sulfonic acid.

Example 7

Secondary Esterification Test

The sulfonic acid, the test equipment and the process employed in this example were the same as example 1. The effect of the esterification time on the content of the disodium salt was studied in the test.

Figure 11:
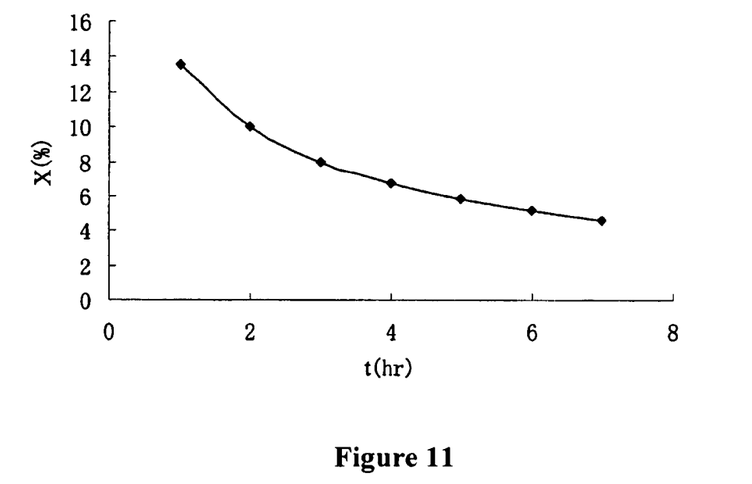
FIG. 11 shows the effect of the esterification time on the content of the disodium salt in the product in example 7, in which the esterification lasts for 1, 2, 3, 4, 5, 6 and 7 hours, respectively. The symbol t (hr) is the esterification time and X (%) is the content of the disodium salt.

Methanol was used as esterifying agent in an amount of 100% based on the weight of the sulfonic acid (bleached). The esterification was carried out under reflux for 1, 2, 3, 4, 5, 6 and 7 hours, respectively. The result is shown in FIG. 11.

The experiment result shows that the long esterification time can decrease the content of the disodium salt. However, the esterification becomes difficult when the content of the disodium salt is reduced to 5%.

Example 8

Neutralization Test

The sulfonic acid, the test equipment and the process employed in this example were the same as example 1. The effect of the neutralization temperature on the content of the disodium salt was studied in the test.

Figure 12:
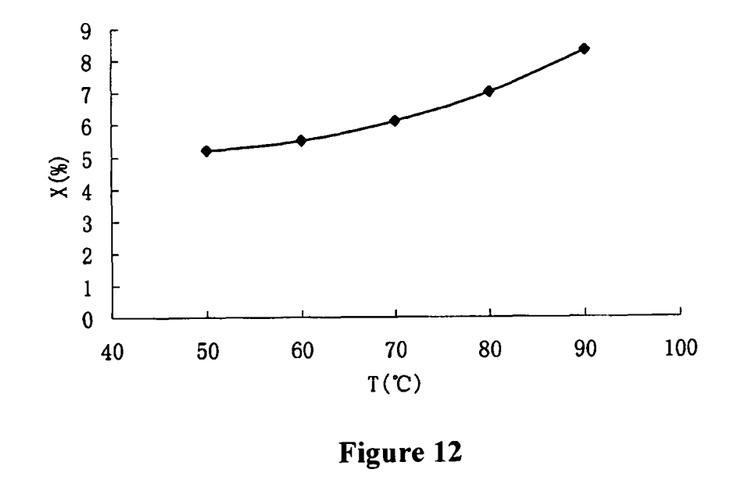
FIG. 12 shows the content of the disodium salt in example 8 after neutralization with a base at a temperature of 50° C., 60° C., 70° C., 80° C. and 90, respectively, wherein T (° C.) is the temperature and X (%) is the content of the disodium salt.

The base used in the neutralization was a 15% solution of sodium hydroxide in methanol. The pH of the sulfonate was controlled to 8. The neutralization was carried out at a temperature of 40° C., 50° C., 60° C., 70° C., 80° C. and 90° C., respectively. The result is shown in FIG. 12.

The experiment result shows that the low temperature lowers the content of the sulfonate, and the temperature below 50° C. may make the process unrealisable. Thus, it is suitable to control the neutralization temperature between 50° C. and 60° C.

Example 9

Neutralization Test

The sulfonic acid, the test equipment and the process employed in this example were the same as example 1. The effect of the base concentration on the content of the disodium salt during the neutralization was studied in the test.

Figure 13:
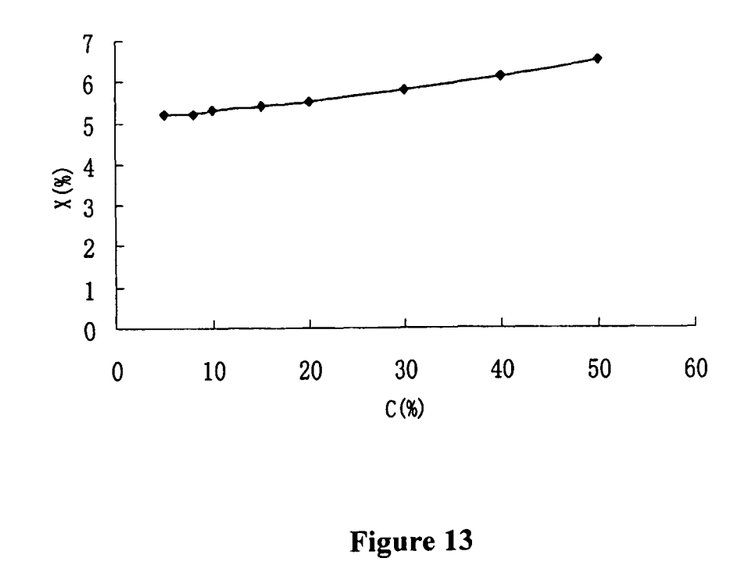
FIG. 13 shows the content of the disodium salt in example 9 after neutralization at 60° C. with a solution of sodium hydroxide at a concentration of 5%, 8%, 10%, 15%, 20%, 30%, 40% and 50%, respectively, wherein C (%) is the concentration of the sodium hydroxide solution and X (%) is the content of the disodium salt.

The neutralization was carried out at 60° C. with a sodium hydroxide solution at a concentration of 5%, 8%, 10%, 15%, 20%, 30%, 40% and 50%, respectively, followed by a test of the content of the disodium salt. The result is shown in FIG. 13.

It can be seen from the data that a dilute solution of a base is favourable for the product quality. The too high concentration of the base may result in the increased content of the disodium salt in the neutralized product, while a too dilute solution may make the drying difficult. Thus, the base is advantageously used in a concentration of 10%-30%.

The invention claimed is:

1. A process for preparing alpha-sulfo-fatty acid ester salt surfactants, comprising the following steps:
    (1) sulfonation: sulfonating a fatty acid ester with sulphur trioxide to prepare a crude sulfonic acid;
    (2) bleaching: bleaching the crude sulfonic acid obtained in step (1) by using hydrogen peroxide as bleaching agent;
    (3) secondary esterification: subjecting the product of step (2) to a secondary esterification using an alcohol as esterifying agent;
    (4) neutralization: neutralizing the product of step (3) with a base; and
    (5) drying: drying the product of step (4) to obtain a powdery product,
    wherein the bleaching agent is fed by means of a spray and is mixed homogeneously using a rotor film-scrapping shear mixer to ensure sufficient reaction, and wherein the bleaching is cooled down by a cold air blast or room-temperature blast to remove heat generated in the process.

2. The process for preparing alpha-sulfo-fatty acid ester salt surfactants as described in claim 1, characterized in that the sulfonation in step (1) is carried out at a temperature of 75° C.-85° C. with the molar ratio of a fatty acid methyl ester to sulphur trioxide between 1:1.15 and 1:1.35; the first aging lasts for 40-60 minutes at a temperature of 80° C.-90° C., and the second aging lasts for 30-60 minutes at a temperature of 70° C.-80° C.

3. The process for preparing alpha-sulfo-fatty acid ester salt surfactants as described in claim 1, characterized in that the sulfonation in step (1) is carried out at a temperature of 80° C. with the molar ratio of a fatty acid methyl ester to sulphur trioxide of 1:1.25; the first aging lasts for 40 minutes at a temperature of 80° C.-90° C., and the second aging lasts for 30-40 minutes at a temperature of 70° C.-80° C.

4. The process for preparing alpha-sulfo-fatty acid ester salt surfactants as described in claim 1, characterized in that the sulfonation in step (1) is carried out in a falling film sulfonator 11, which sulfonator consists of fourteen sulfonating tubes with an inner diameter of 30 mm and a length of 6000 mm; a liquid fatty acid methyl ester from a pipe 16 is distributed homogeneously on the wall of each sulfonating tube, and a mixture of sulphur trioxide and air is injected into each tube and flow downward along the tube together with the liquid, during which process the fatty acid ester are sulfonated with sulphur trioxide; the sulfonic acid mixture exits from the bottom of the reactor and enters a gas-liquid separator 12 through a pipe 17, where the remaining gas is separated for absorption by an alkali liquor in a high-pressure electrostatic demister; the sulfonic acid liquid flow through a pipe 18 into aging reactors 13 and 14.

5. The process for preparing alpha-sulfo-fatty acid ester salt surfactants as described in claim 1, characterized in that the bleaching in step (2) is carried out at 50-150° C. with oxydol as bleaching agent, with a concentration of 25%-50% and in an amount of 3-20% based on the weight of the sulfonic acid.

6. The process for preparing alpha-sulfo-fatty acid ester salt surfactants as described in claim 1, characterized in that the bleaching in step (2) is carried out at 75-90° C. with oxydol as bleaching agent, with a concentration of 35% and in an amount of 5-8% based on the weight of the sulfonic acid.

7. The process for preparing alpha-sulfo-fatty acid ester salt surfactants as described in claim 1, characterized in that, in the bleaching of step (2), the reactant materials are fed in a spray header along with cold air or room-temperature air, and then homogeneously mixed by a multi-stage perforated plate and a rotor film-scrapping shear mixer for sufficient reaction, the cold air or room-temperature air being used for removing the heat generated from the process; the bleaching unit consists of a fan 20, freezers 21 and 25, a primary mixing tank 22, a secondary mixing tank 23 and a gas-mass separator 24; the sulfonic acid from an aging reactor 14 is transported through a pipe 25 to a heat exchanger 30, where it is cooled down; air from the fan 20 is fed through a pipe 31 to the freezer, where it is cooled down, and then to a spray header 28 through a pipe 32; the cooled air, hydrogen peroxide from a pipe 27 and the sulfonic acid from a pipe 26 are spray-mixed in the spray header of the primary mixing tank; the mixture is further mixed by a multi-stage perforated plate 29 and cooled down by a lower tube array 38, then transported through pipes 34 and 35 to the secondary mixing tank 23, where it is mixed homogeneously by a multi-stage rotor film-scrapping shear mixer 33 for sufficient reaction; the mixture is finally transported through a pipe 37 to the gas-mass separator 24, in which the air is discharged from 40 to obtain a paste product.

8. The process for preparing alpha-sulfo-fatty acid ester salt surfactants as described in claim 1, characterized in that the alcohol used as esterifying agent in the secondary esterification of step (3) is in an amount of 75%-200% based on the weight of the sulfonic acid, and the secondary esterification is carried out under reflux for 1-6 hours.

9. The process for preparing alpha-sulfo-fatty acid ester salt surfactants as described in claim 1, characterized in that the alcohol used as esterifying agent in the secondary esterification of step (3) is methanol in an amount of 100% based on the weight of the sulfonic acid, and the secondary esterification is carried out under reflux at a temperature of 80° C. for 5-6 hours.

10. The process for preparing alpha-sulfo-fatty acid ester salt surfactants as described in claim 1, characterized in that the secondary esterification is carried out in a continuous way in a reflux reactor; the secondary esterification unit used consists of a mixer 41, reactors 42, 43 and 44, and condensers 45, 46 and 47; the bleached sulfonic acid from a pipe 48 and methanol from a pipe 49 are fed together to the mixer 41; the mixture is heated and sent to the reactors 42, 43 and 44 through pipes 50, 51 and 52, respectively, for the secondary esterification; the evaporated methanol is refluxed by the condensers 45, 46 and 47; the secondary esterification is carried out in a continuous way, i.e., the reactant materials are fed in continuously from the top of the reactor, and the product materials are discharged continuously from the bottom of the reactor; the product is finally sent through a pipe 53 to a cooler 56 for cooling.

11. The process for preparing alpha-sulfo-fatty acid ester salt surfactants as described in claim 1, characterized in that the base used in the neutralization of step (4) is an aqueous or alcoholic solution of sodium hydroxide or potassium hydroxide with a concentration of 5-50%, and the neutralization is carried out at a temperature of 40° C.-80° C., the neutralized sulfonate salt being controlled to a pH of 7-8.

12. The process for preparing alpha-sulfo-fatty acid ester salt surfactants as described in claim 1, characterized in that the base used in the neutralization of step (4) is an aqueous or alcoholic solution of sodium hydroxide or potassium hydroxide with a concentration of 10-30%, and the neutralization is carried out at a temperature of 50° C.-60° C., the neutralized sulfonate salt being controlled to a pH of 7-8.

13. The process for preparing alpha-sulfo-fatty acid ester salt surfactants as described in claim 1, characterized in that the product of step (3) and the base in the neutralization of step (4) are fed by means of spray.

14. The process for preparing alpha-sulfo-fatty acid ester salt surfactants as described in claim 1, characterized in that the product of step (3) and the base in the neutralization of step (4) are mixed homogeneously by using a rotor film-scrapping shear mixer in order to ensure sufficient reaction.

15. The process for preparing alpha-sulfo-fatty acid ester salt surfactants as described in claim 1, characterized in that the neutralization of step (4) is cooled down by cold air blast or room-temperature air blast to remove the heat generated in the process.

16. The process for preparing alpha-sulfo-fatty acid ester salt surfactants as described in claim 1, characterized in that, in the neutralization of step (4), the product of step (3) and the base are fed in a spray header along with cold air or room-temperature air, and then homogeneously mixed by a multi-stage perforated plate and a rotor film-scrapping shear mixer for sufficient reaction, the cold air or room-temperature air being used for removing the heat generated from the process; the neutralization unit consists of a fan 60, freezers 61 and 78, a primary mixing tank 62, a secondary mixing tank 63 and a gas-mass separator 64; air from the fan 60 is sent through a pipe 65 to the freezer, where it is cooled down, and then sent through a pipe 76 to a spray header 70 of the primary mixing tank, along with an alkali liquid from a pipe 67 and the esterified sulfonic acid from a pipe 57; the mixture is spray-mixed and further cooled down by passing through a multi-stage perforated plate 68 and a lower tube array 69; the cooled mixture is then transported through a pipe 72 to the secondary mixing tank 63, in which it is mixed homogeneously by a multi-stage rotor film-scrapping shear mixer 73 with cooling by the cooled air from a pipe 77; the neutralized mixture is transported through a pipe 74 to the gas-mass separator 64, in which the air is discharged from 75 to obtain a paste product.

17. The process for preparing alpha-sulfo-fatty acid ester salt surfactants as described in claim 1, characterized in that the drying in step (5) is carried out in a rotary thin-film evaporator at a temperature of 50° C.-90° C. under vacuum pressure of 50-200 mmHg.

18. The process for preparing alpha-sulfo-fatty acid ester salt surfactants as described in claim 1, characterized in that a drying unit used in step (5) consists of a rotary thin-film evaporator 81, a conveying pump 82, a storage tank 83, a screw discharging machine 84, a vacuum pump 85 and a condenser 88; the neutralized paste is sent through the pipe 86 to the storage tank 83, and then to the dryer vessel through a pipe 87, and the dried product is discharged through the screw discharging machine 84.

19. The process for preparing alpha-sulfo-fatty acid ester salt surfactants as described in claim 1, characterized in that a multi-stage rotor film-scrapping shear mixer used in the bleaching of step (2) consists of a stator air plate and a rotor film-scrapping blade, with the stage number in the range of 3-50.

20. The process for preparing alpha-sulfo-fatty acid ester salt surfactants as described in claim 1, characterized in that a multi-stage rotor film-scrapping shear mixer used in the neutralization of step (4) consists of a stator air plate and a rotor film-scrapping blade, with the stage number in the range of 3-50.

* * * * *

UNITED STATES PATENT AND TRADEMARK OFFICE
CERTIFICATE OF CORRECTION

PATENT NO.       : 8,604,226 B2                                            Page 1 of 1
APPLICATION NO. : 12/226754
DATED            : December 10, 2013
INVENTOR(S)      : Hongcai Li It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 270 days.

Signed and Sealed this

Twenty-second Day of September, 2015

Michelle K. Lee
*Director of the United States Patent and Trademark Office*